US006670118B2

(12) United States Patent
Hirschman

(10) Patent No.: US 6,670,118 B2
(45) Date of Patent: *Dec. 30, 2003

(54) METHOD FOR TREATING PAPILLOMAVIRUS INFECTIONS

(75) Inventor: Shalom Z. Hirschman, Riverdale, NY (US)

(73) Assignee: Advanced Viral Research Corp., Hallandale, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/189,172

(22) Filed: Nov. 10, 1998

(65) Prior Publication Data

US 2001/0036920 A1 Nov. 1, 2001

Related U.S. Application Data

(63) Continuation-in-part of application No. 08/923,516, filed on Sep. 4, 1997, now abandoned, which is a continuation-in-part of application No. 08/838,071, filed on Apr. 15, 1997, now abandoned.

(51) Int. Cl.$^7$ ................................................ C12Q 1/68
(52) U.S. Cl. ................................................ 435/6; 435/5
(58) Field of Search ...................... 514/12, 2; 536/22.1; 435/6, 5

(56) References Cited

U.S. PATENT DOCUMENTS 6,303,153 B1 * 10/2001 Friedland et al. ............ 424/529
6,355,226 B1 * 3/2002 Hirschman .................... 424/45

OTHER PUBLICATIONS

Webster et al, 1994, Academic Press, vol. 2, pp. 1013–1026, 1994.*
Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–24, 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.
Medoff, Lawrence R., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Kosaka, K. and Shimada, Y., Infectious Hepatitis, Symposium, pp. 61–74, 1960.
Anderson, Robert H. and Thompson, Ralph M., Treatment of Viral Syndrome with a Lipoprotein–Nucleic Acid Compound (Reticulose), A Report of Five Cases, Virginia Medical Monthly, 84: 347–353, 1957.
Reynolds, Margaret R., Generalized Vaccinia Successfully Treated With Lipoprotein–Nucleic Acid Complex (Reticulose), Archives of Pediatrics, 77:421–422, 1960.
Wegryn, Stanley P., Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia And Chicken Pox, J. Roy. Coll. Gen. Practit., 1970, 19, 182.
Chinnici, Angelo A., Reticulose in Treatment Aids patients, Personal Communication to William Bregman, Jul. 6, 1992.
Cott, Rafael A., Summary of 11 Cases of Viral Infections Treated with Reticulose, Private Communication with Advance Viral Research Corp., 1989.
Cohen, Matthew, The Efficacy of a Peptide–Nucleic Acid Solution (Reticulose) for the Treatment of Hepatitis A and Hepatitis B—a Preliminary Controlled Human Clinical Trial, J. Roy. Soc. Health, Dec., 1992, 266–270.
Mundschenk, David D., In Vitro Antiviral Activity of Reticulose vs Influenaz A, Personal Communication with William Bregman, May 1, 1990.
Resnick, Lionel, Anti–HIV in Vitro Activity of Two Samples of Peptide–nucleic Acid Solution, Personal Communication with Dr. Bernard Friedland, Dec. 22, 1989.
Friedland, Bernard, In Vitro Antiviral Activity of a Peptide––Nucleic Acid Solution Against the Human Immunodeficiency Virus and Influenza A Virus, J. Roy. Soc. Health, Oct. 1991, 170–171.
Brazier, Anne D., Method for in Vitro Antiviral Evaluation Human Immunodeficiency Virus (HIV), Personal Communication with Dr. Bernard Friedland, Oct. 4, 1989.
Behbehani, Abbas M., Haberman Sol and Race, George J, The Effect of Reticulose on Viral Infections of Experimental Animals, Southern Medical Journal, Feb., 1962, 185–188.
Treatment of Viral Diseases with A Lipo–protein Nucleic Acid Complex (Reticulose)—A Clinical Study, Scientific Exhibit: Virginia State Medical Society Meeting, Washington D.C., Nov., 1957.
Kempe, Henry C., Fulginiti, Vincent A., and Vincent, Leone St., Failure to Demonstrate Antiviral Activity of Reticulose, Diseases of Children, vol. 103, No. 5, 655–657, 1962.
Sanders, Murray, Controlled Animal Studies with Reticulose Illustrating the Interference of Lipoprotein–Nucleic Acid Complex in the Experimental Animal Infected with Human Pathogenic Viral Entities, Southern Medical Association Scientific Exhibit, Dallas, Texas, Nov., 1961.

* cited by examiner

Primary Examiner—Ali Salimi
(74) Attorney, Agent, or Firm—Cohen, Pontani, Lieberman & Pavane

(57) ABSTRACT

The present invention discloses a method of treatment for patients having lesions resulting from papillomavirus infections by topically administering Product R, a peptide-nucleic acid preparation, to the lesions.

3 Claims, No Drawings

METHOD FOR TREATING PAPILLOMAVIRUS INFECTIONS

CROSS-REFERENCE TO RELATED APPLICATIONS

This application is a continuation-in-part of application Ser. No. 08/923,516, filed Sep. 4, 1997, now abandoned, which is a continuation-in-part of the application Ser. No. 08/838,071, filed by Shalom Z. Hirschman on Apr. 15, 1997, entitled "A Method For Treating Papillomavirus Infections", now abandoned.

BACKGROUND OF THE INVENTION

1. Field of the Invention

The present invention relates to a method for using Product R as hereinafter defined to treat patients infected with papillomaviruses.

II. Description of the Related Art

Treatment of viral diseases in humans is a major focus of medical science. While some progress has been made, viral infections are still among the diseases most difficult to treat. Despite growing understanding of viral diseases along with improved techniques for detecting and treating them, few antiviral drugs have proved effective. Some viral diseases such as HIV are life threatening; others such as herpes simplex virus and influenza virus continue to cause severe problems. Further, new viral diseases constantly appear as an inevitable consequence of evolution. Thus, searching for a novel and effective way of treating viral diseases remains imperative and challenging.

Product R[1] emerged as an antiviral product in the 1930's. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

[1]. The agent is known under the trademark "Reticulose", a trademark of Advanced Viral Research Corp.

Despite these early promising clinical reports, systematic studies have rarely been performed to establish clinical utility. Optimum dosages of Product R for treating viral infections an as indicated above have been poorly investigated. In fact, most of the clinical reports lacked necessary controls and statistically sufficient samples for evaluating the effectiveness of Product R. Note, two earlier publications challenged that Product R failed to demonstrated antiviral activity. In light of this controversy, the present status of the art of using Product R in treating viral infections remains questionable. Close examination of the development history of Product R reveals no meaningful pattern that could be followed to designate a treatment for a particular viral infection, for viruses causing those infections are extremely diversified in their genetic traits or/and pathogenesis. In addition, earlier clinical applications described Product R only as an agent to be administered alone. Product R has never been suggested to be applied in combination with other antiviral drugs; nor has Product R been administered for a period longer than about two months. Given the limits of prior art, developing new treatment strategies using Product R is desirable.

In developing an antiviral agent, it is well known that inhibitory activity of an antiviral agent against a particular virus cannot be equated with its inhibitory effect against another virus. For example, acyclovir has proved to be specifically effective against herpes simplex 1 and 2 but not against cytomegalovirus (CMV), even though both HSV and CMV belong to the same herpesvirus family, sharing certain genetic features. The specificity of acyclovir rests on the activity of the thymidine kinase gene unique to HSV 1 and 2, indicating that a distinctive feature of each individual virus forms a basis for developing an antiviral agent specifically against this very virus. In other words, treatment of a viral infection using a certain antiviral agent does not necessarily indicate that the same agent will produce the same effect when used for treating other viral infections. The genetic diversity of viruses further mandates that an attempt to be made to discern the effectiveness of a new application of an antiviral agent to a different virus.

An antiviral agent usually interacts with molecules involved in different stages of viral infections: in early events such as adsorption, penetration (internalization), and uncoating; in virus replication characteristic for each virus genome and components of the nucleoprotein complex; and in the chemistry of metabolic pathways. The best targets for inhibition by an antiviral agent are molecules serving a function unique to the virus, with no analogous counterpart in host cells. In order to identify the virus-specific molecule with which a putative antiviral agent interacts, it is important to characterize viruses in terms of particle and genome structure, as well as to define specific biochemical events that occur in infected cells. Although progress has been made in discovering molecules necessary for virus adsorption, replication and metabolism, current knowledge remains insufficient to explain many aspects of these events. Consequently, not every antiviral agent's function is fully defined in terms of its interaction with a target virus through one or a series of the indicated events; much less is understood where an antiviral agent is employed to treat a new viral infection, especially if the antiviral agent has been poorly characterized. Without the knowledge of a virus' genetic traits and the chemical properties of an antiviral agent, treatment of a viral infection becomes unpredictable.

SUMMARY OF THE INVENTION

The object of this invention therefore is to develop a method for treating patients infected by papillomaviruses, or exhibiting papillomavirus associated symptoms, or having antibodies against papillomaviruses, by administering parenterally or topically to the patients Product R, an antiviral agent composed of peptides and nucleic acids.

Animal papillomaviruses are associated with purely squamous epithelial proliferative lesions (warts) which can be cutaneous or can involve the mucosal squamous epithelium from the oral pharynx, the esophagus, or the genital tract. Some cutaneous human papillomaviruses (HPVs) play an active role in the occurrence of squamous cell carcinomas, a type of skin cancer, that arise in the warty lesions of a rare dermatological disorder, epidermodysplasia vervruciformis (EV). Some genital-tract HPVs produce genital warts and they are predominant among HPVs that infect other mucosal sites such as the respiratory tract, the oral cavity, and the conjunctiva. It is now clear that HPV infections of the genital tract are among the most prevalent sexually transmitted infections and are etiologically related to some squamous cell carcinomas of the genital tract, most notably of the uterine cervix, a major human cancer. World-wide, about 500,000 new cases of invasive cancer of the cervix are diagnosed annually. In developing countries, cancer of the cervix is the most frequent female malignancy and constitutes about 24% of all cancers in women. In developed countries, it ranks behind cancers of the breast, lung, uterus, and ovaries and accounts for 7% of all female cancers.

Patients with acquired immunodeficiency syndrome (AIDS) or human immunodeficiency virus (HIV) infections are beset by many different kinds of infections that are not commonly seen in immunocompetent patients. These infections are termed opportunistic infections. One of the sexually transmitted infections that are common in patients with AIDS is genital warts caused by several different types of HPV.

In general, papillomaviruses are small, nonenveloped viruses with an icosahedral symmetry, 72 capsomere, and a double-strand circular DNA genome of about 8,000 bp. One characteristic of the genomic organization of papillomaviruses is that all of the open reading frames of the genome are located on one strand, indicating that all of the viral genes are located on one strand. All papillomaviruses have a similar genetic organization. The viral genome is divided into an early region which encodes the genes required for viral DNA replication and cellular transformation, a late region that codes for the capsid proteins, and a regulatory region that contains the origin of replication and many of the control elements for transcription and replication.

Papillomaviruses have two modes of viral DNA replication. The first likely occurs in the cells of the lower portion of the epidermis, including the basal cells, as well as in the dermal fibroblasts in fibropapillomas. In these cells, the viral DNA is apparently maintained as a stable multicopy plasmid. The viral genomes replicate an average of once per cell cycle during S-phase in synchrony with the host cell chromosome and may be faithfully partitioned to the daughter cells. This type of DNA replication ensures a persistent and latent infection in the stem cells of the epidermis. The second type of DNA replication is vegetative DNA replication, which occurs in the more differentiated epithelial cells of the papilloma. The mechanisms regulating the switch from plasmid maintenance to vegetative viral DNA replication are not known. The switch may involve the presence or absence of controlling cellular factors in differentiating keratinocytes.

The genomes of the papillomaviruses contain multiple cis regulatory elements and encode several transcriptional factors that modulate viral gene expression. Papillomavirus transcription is complex due to the presence of multiple promoters, alternate and multiple splice is patterns, and the differential production of MRNA species in different cells. The transcription is tightly regulated in infected cells.

In addition to papillomavirus' distinctive genome structure, modes of replication and transcription, two major biologic characteristics also set papillomavirus apart from other viruses. First, papillomarviruses have a high degree of species specificity. There are no known examples of natural transmission of HPVs to other species. Papillomaviruses also display a marked degree of cellular tropism. HPVs infect only surface squamous epithelia of the skin or mucosa producing for the most part benign epithelial tumors. The productive infection of cells by the papillomaviruses can be divided into early and late stages. These stages are linked to the differentiation state of the epithelial cell. The interaction between cellular proteins with elements of the regulatory region of the viral genome provides the molecular basis of the cellular tropism of HPVs. Specific viral types appear to have a preference for either cutaneous or mucosal types. For example, HPV-11 does not readily infect cutaneous epithelium from other body sites but can infect mucosal epithelium of either the genital or the respiratory tract.

Second, a fundamental property of the papillomaviruses is induction of cellular proliferation and transformation. The most common clinical manifestation of infection with papillomaviruses is the production of warts, which are benign tumors. The progression of benign papillomas to invasive cancers can be characterized as follows: 1) only some of the virus types may have oncogenic potential; 2) the time interval between the initial infection and the development of invasive cancers may be long; in the case of human genital-tract cancers, this interval may span several decades; 3) cofactors are required for the progression to malignancy. One interesting feature of papillomavirus transformed cells is that the papillomaviral DNA is often maintained as a multicopy plasmid, and that integration of the viral genome is not required for either the initiation or maintenance of the transformed state.

Little is known concerning virus attachment, receptors, virion entry, uncoating, assembly, or release.

Various treatments of papillomaviruses include application of caustic agents, cryotherapy, application of an inhibitor of DNA synthesis, surgical therapy and immunotherapy have been tried, but effectiveness of these therapies is difficult to assess because of spontaneous regression on the one hand and recurrence on the other.

It has now been discovered that Product R is useful in treating patients identified as having papillomavirus associated symptoms, as well as patients identified as infected by or carrying papillomavirus or having antibodies to papillomavirus. The present invention relates to a method for treating the identified patients by administering parenterally to the patients an effective papillomavirus treatment amount of Product R from about 5 microliters to about 40 microliters per kilogram of body weight per day in a sterile injectable formulation.

DETAILED DESCRIPTION OF THE PRESENTLY PREFERRED EMBODIMENTS

The present invention discloses the use of Product R as a method of treating patients identified as having papillomavirus associated symptom(s) by administering parenterally an effective dose of Product R.

The invention also discloses the method of treating a patient infected by or carrying papillomaviruses with Product R to inhibit the replication of the papillomaviruses in infected patient cells and to prevent papillomavirus infection from developing in humans infected with the papillomaviruses.

The invention further discloses the method of treating a patient carrying antibodies against papillomaviruses by administering parenterally effective dose of Product R.

As used herein, Product R is the product produced according to either of the following methods.

Method I For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C.

The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with is Product R are cooled and washed.

All quantities are subject to plus or minus 2.5% variation for pH, volume, and analytical adjustments.

For the above papillomavirus infections including patients with AIDS or HIV infections, whether the patient exhibits papillomavirus associated symptoms, infections or antibody responses, a suitable effective dose of Product R will be in the range of from about 5 microliters to about 40 microliters per kilogram of body weight per day, preferably in the range of about 10 microliters to about 25 microliters per kilogram of body weight per day. Most preferably Product R is administered in an amount of about 30 microliters per kilogram of body weight per day for about one week, followed by about 15 microliters per kilogram of body weight per day in a sterile injectable formulation until the patient becomes asymptomatic or viral load becomes undetectable. The desired dose may be administered as two, three or more sub-doses at appropriate intervals, generally equally spread in time, throughout the day. Preferably, the full daily dose is administered in one administration.

Product R may be administered by any suitable injection route including, but not limited to intravenously, intraperitoneally, subcutaneously, intramuscularly, and intradermally, etc. The presently preferred route of administration is intramuscularly. It will be appreciated that the preferred route may vary with, for example, the condition and age of the recipient.

Product R may be used in therapy in conjunction with other medicaments including corticosteroid, gamma globulin, glucose, or vitamins, antiviral agents such as interferon or interleukin, etc.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

The following examples further illustrate the operation, but do not in any way limit the scope, of the present invention.

EXAMPLE I

Five patients, two females and three males, were treated with Product R by topically applying Product R on the lesions which are identified as viral vegetative type warts caused by human papillomavirus (Condyloma acuminatum). Most of these lesions were condylomas acuminatum of short evolution. Product R as defined by the process of manufacture was applied topically to the lesions in amounts that adequately cover the lesions twice per day (morning and evening) for two weeks (about 28 applications). At the end of the treatment period, the lesions were no longer observed.

EXAMPLE II

Eight patients who were diagnosed as having genital papillomavirus infections were treated with Product R also by topically administering Product R once a week for four weeks. At the end of the treatment period, no visible lesion could be observed in seven of these patients. The treatment results were further confirmed by the subsequent biopsy analysis, which indicated that the tissues were no longer infected.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method for reducing condyloma acuminatum lesion in a patient having condyloma acuminatum infection, comprising topically administering Product R to said patient in an effective condyloma acuminatum lesion treatment amount that adequately covers said lesion, wherein said Product R is made by a process comprising the steps of:

a mixing about 34 to about 36 grams of casein, about 16.7 to about 17.5 grams of beef peptone, about 21.5 to about 22.6 grams of ribonucleic acid (RNA), about 3.17 to about 3.33 grams of bovine serum albumin, about 16 to 17 grams of sodium hydroxide in water to form a water suspension or solution;

b autoclaving the mixture from said step a until RNA is completely digested;

c cooling the product from said step b, said cooled product comprising solids;

d removing said solids from the product from said step c;

e adding water to the product from said step d to bring the final volume to about 5 liters; and f adjusting the pH of the product from said step e to a physiologically acceptable pH range.

2. The method of claim 1, further comprising topically administering Product R to said lesion twice a day for at least two weeks.

3. The method of claim 1, further comprising topically administering Product R to said lesion once a week for at least four weeks.

* * * * *